United States Patent
Schrenk et al.

(12) 
(10) Patent No.: US 7,186,382 B2
(45) Date of Patent: Mar. 6, 2007

(54) MICROCHIP APPARATUS

(75) Inventors: Walter Schrenk, Karlsbad (DE); Tobias Preckel, Waldbronn (DE)

(73) Assignee: Agilent Technologies, Inc., Palo Alto, CA (US)

( * ) Notice: Subject to any disclaimer, the term of this patent is extended or adjusted under 35 U.S.C. 154(b) by 657 days.

(21) Appl. No.: 10/121,495

(22) Filed: Apr. 12, 2002

(65) Prior Publication Data

US 2002/0185379 A1 Dec. 12, 2002

(30) Foreign Application Priority Data

Jun. 7, 2001 (EP) .................................. 01113937

(51) Int. Cl.
  *B01L 3/02* (2006.01)
  *B01L 11/00* (2006.01)
  *B32B 5/02* (2006.01)
  *B32B 27/04* (2006.01)
  *B32B 27/12* (2006.01)

(52) U.S. Cl. ........................ 422/100; 422/50; 422/101; 422/102; 422/103; 422/104; 422/68.1; 422/82; 436/43; 73/1.01; 73/1.02

(58) Field of Classification Search ................ 422/50, 422/100, 101, 102, 103, 104, 68.1, 82; 436/43; 73/1.01, 1.02

See application file for complete search history.

(56) References Cited

U.S. PATENT DOCUMENTS

| | | | | |
|---|---|---|---|---|
| 5,980,704 A | | 11/1999 | Cherukuri et al. | 204/269 |
| 6,033,628 A | * | 3/2000 | Kaltenbach et al. | 422/68.1 |
| 6,090,251 A | | 7/2000 | Sundberg et al. | 204/453 |
| 6,110,332 A | * | 8/2000 | Swierkowski | 204/242 |
| 6,149,787 A | * | 11/2000 | Chow et al. | 204/451 |
| 6,447,661 B1 | * | 9/2002 | Chow et al. | 204/453 |
| 6,572,828 B1 | * | 6/2003 | Potyrailo et al. | 422/130 |
| 6,692,708 B2 | * | 2/2004 | Chandler, Jr. | 422/225 |

OTHER PUBLICATIONS

Persichini, C., Examiner. European Search Report, Application No. EP 01 11 3937, dated Nov. 16, 2001.

* cited by examiner

*Primary Examiner*—Brian Sines

(57) ABSTRACT

A system and method for providing an improved microchip measurement apparatus comprising an external reservoir connected via an input line and output line to a well disposed on the microchip. The reservoir and well may be sealed and a pump connected to the input line so as to enable a continuous flow of liquid from the reservoir to the well. In addition, the volume of liquid in the well may be kept constant, thereby improving the overall measurement accuracy.

19 Claims, 6 Drawing Sheets

MICROCHIP APPARATUS

The present invention concerns an improved microchip apparatus. More specifically, the present invention concerns a new apparatus for introducing samples and reagents to a microchip.

The use of microchip type devices for chemical analysis is well known. Microchip based analytical instruments are commercially available, such as Agilent's Bio Analyser 2100. In the Bio Analyser samples and reagents are introduced to the microchip manually using a pipette or syringe.

FIG. 1 shows a current microchip type device. The sample or reagent 1 is deposited into reservoir 2 located on microchip 3 with syringe 4. The sample or reagent is then caused to flow through microchannel 5 with known techniques, such as electrophoresis or electroosmosis.

A problem with the above device is that the sample/reagent must be manually deposited into the reservoir. Often a microchip will contain many tens of reservoirs, thus this process is time consuming and often inaccurate.

A further problem exists with this current method in that while the last reservoirs on the chip are being filled some of sample/reagent deposited into the first reservoir may have evaporated. This can have the negative effect of altering some of the physical or chemical parameters of the sample/reagent, such as the temperature or pH, ultimately adversely effecting the accuracy of the analytical data.

It is an object of the present invention to overcome the above-mentioned technical problems.

The present invention overcomes these problems by providing an apparatus in which the sample/reagent is continuously circulated through the reservoir thus maintaining a constant volume of liquid in the reservoir.

According to the present invention there is provided a measurement apparatus comprising: a microchip having a well disposal therein, said well being capable of containing a volume of a liquid, and a microchannel connected to said well and arranged to allow said liquid to flow there through, characterised in that said apparatus further comprises a reservoir disposal externally to said microchip, an input line connecting said reservoir to said well and arranged to allow liquid to flow from said reservoir to said well, an output line connected to said well and arranged to allow liquid to flow from said well, and pump means disposed along said input line and arranged to facilitate said flow of liquid from said reservoir to said well and said flow of liquid from said well in a manner such that the volume of liquid contained within said well remains substantially constant.

Advantageously, by keeping a constant volume in the reservoir, the physical parameters of the reagent are held substantially constant.

While the principle advantages and features of the invention have been described above, a greater understanding and appreciation of the invention may be obtained by referring to the drawings and detailed description of a preferred embodiments, presented by way of example only, in which.

Figure 1:
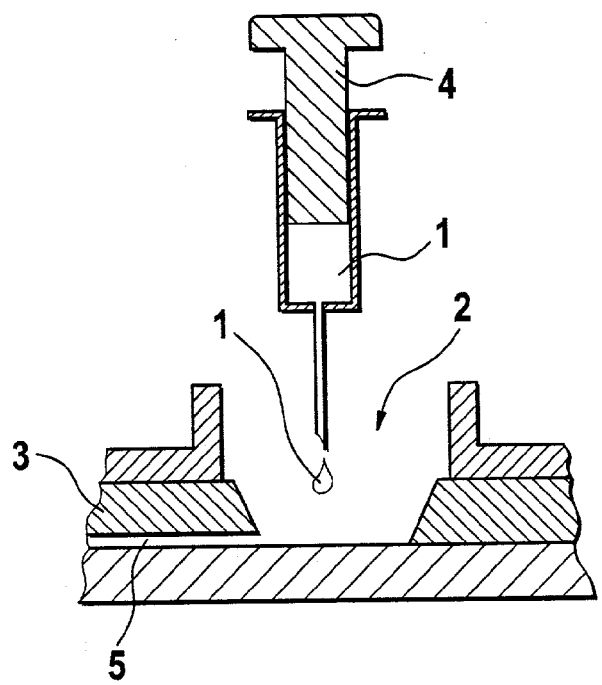
Figure 2:
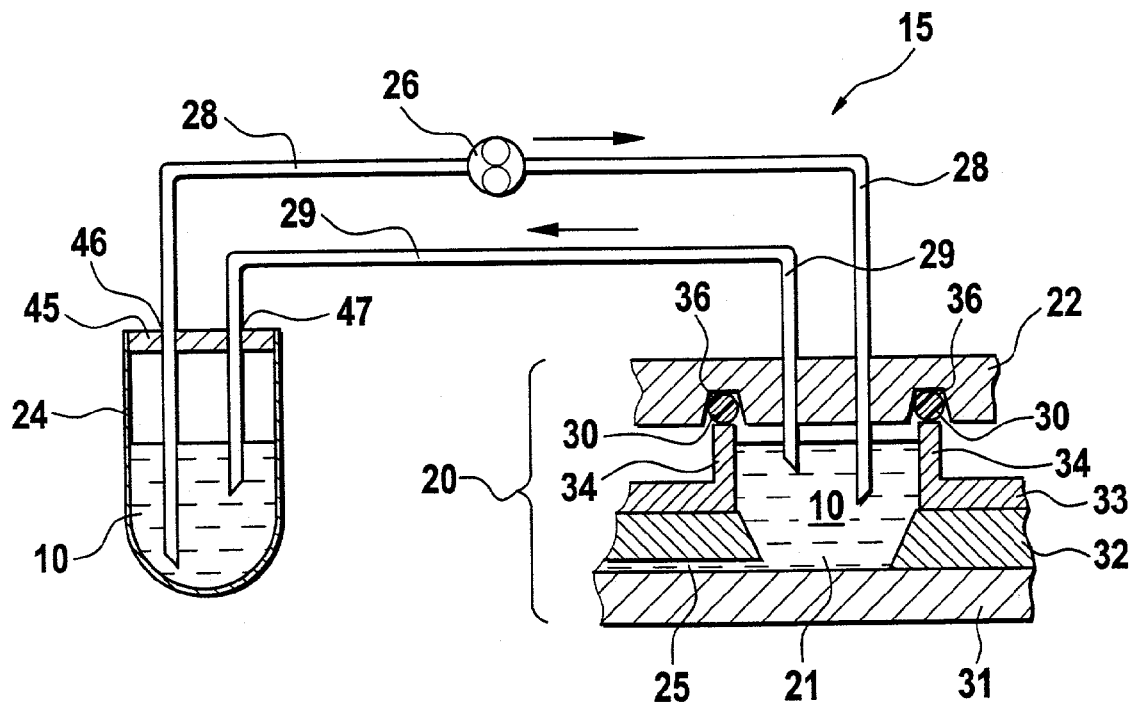
FIG. 2 shows a schematic of the microchip and pump arrangement.

In FIG. 2 the microchip and pumping system 15 comprises microchip 20, pump means 26, external reservoir 24, and input and output lines 28 and 29 respectively.

The microchip is of the type known in the art and as such will only be briefly described below. Microchip 20 comprises a lower plate 31 and an upper plate 32, which are arranged to form microchannel 25. A reservoir or well 21 is formed in the upper plate. The diameter of the reservoir is typically 5 mm, however, as will be appreciated, the diameter can be varied according to the specific application. A microchip carrier 33 is attached to the upper plate and has side walls 34, which further extend the height of the reservoir.

According to an aspect of the present invention, the microchip includes a cover plate 22 disposed over the top of the reservoir. An O-ring 30 is placed between the cover plate and the side walls 34 of the microchip carrier to from a substantially airtight seal between the cover plate and the microchip carrier. The cover plate preferably includes a groove 36 in which the O-ring is placed.

Also disposed within the cover plate are an inlet aperture 41 and an outlet aperture 42 arranged to receive input line 28 and output line 29 respectively. Apertures 41, 42 are arranged so that when lines 28, 29 are inserted, a substantially airtight seal is established between the apertures and the lines. Preferably, this is achieved by using some type of flexible rubber tubing for input and output lines.

External reservoir 24, which contains a volume reagent or sample is located at a convenient distance from the microchip and includes a lid 45 which when placed on the reservoir forms a substantially airtight seal with the reservoir. The lid has disposed therein an output aperture 46 and an input aperture 47. Similar to the arrangements described above for the microchip cover plate, the lid apertures are arranged to receive the input and output lines 28, 29 in such a way as to maintain an air-tight volume within the reservoir.

A pump means 26 is located along input line 28 and is arranged to pump liquid from the external reservoir 24 to the microchip well 21. In this embodiment the pump means is a peristaltic pump, however, as will be appreciated, other types of pumps could be used without departing from the scope of the present invention.

Advantageously, by manufacturing an airtight seal within the reservoir and the well a single pump can be used to cause liquid to flow from the reservoir to the well and from the well to the reservoir.

In a further aspect of the invention, the input line 28 extends further into the microchip well than the output line 29. This arrangement ensures that a minimum volume of liquid is pumped into the well before any liquid can be pumped out of the well and back into the reservoir.

In yet a further aspect of the present invention, the input line 28 extends deeper into the external reservoir then the output line 29. This arrangement ensures that liquid from the lower portion of the external reservoir is pumped to the well.

The overall effect of the arrangement of input and output lines described above is that a constant volume is maintained in the well and that a mixing effect occurs in the external reservoir. Advantageously, this mixing effect helps to prevent any setting of the liquid in the reservoir.

Furthermore, the constant exchange of liquid between the well and the reservoir helps to maintain a constant value of the physical parameters, such as temperature, pH and concentration, of the liquid in the microchip well.

Figure 3:
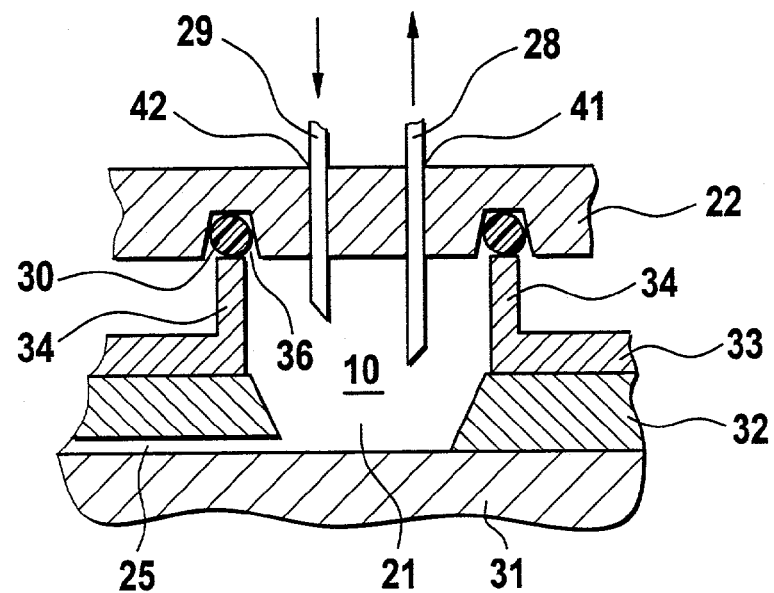
FIG. 3 shows a more detailed view preferred embodiment of the reservoir area of the microchip shown in FIG. 2.

In FIG. 3, where parts also appearing in FIG. 2 bear identical numerical designation, a more detailed view of the microchip and well arrangement is shown in which the input line 28 and output line 29 are extending substantially the same distances into the well.

Figure 4:
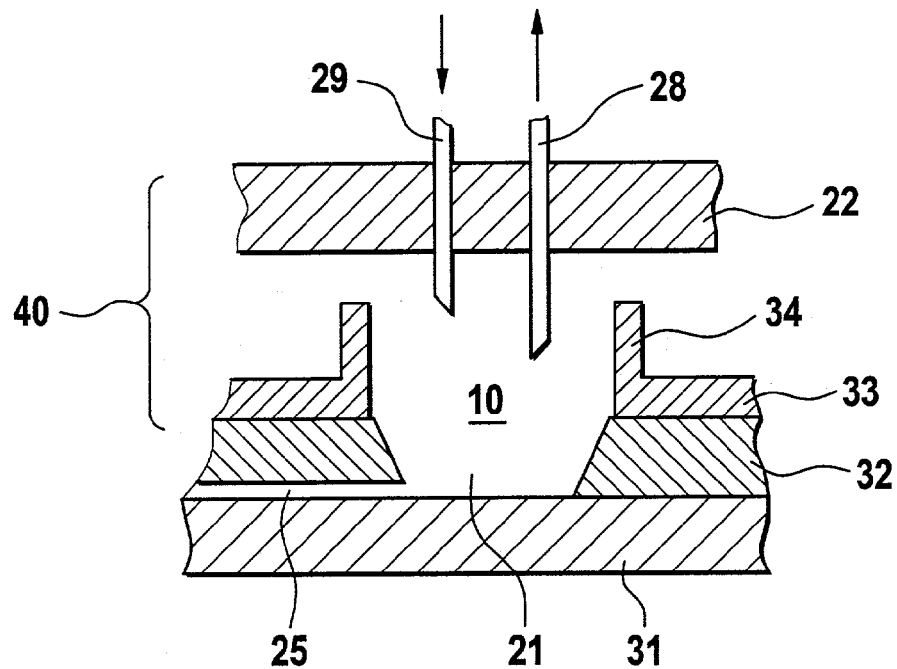
FIG. 4 shows an alternative embodiment of the reservoir area of the microchip.

In FIG. 4, where parts also appearing in FIGS. 2 and 3 bear identical numerical designation, the microchip is shown with the lid 22 not sealed to the well. In this alternative arrangement the well is open to ambient air pressure. In this arrangement movement of liquid to the well is caused by a first pump (not shown) and removal of liquid from the well is caused by a second pump (not shown).

A variety of pumping means can be used with the microchips described in FIGS. 2–4 above. FIGS. 5a–d show some possible pumping arrangements.

Figure 5A:
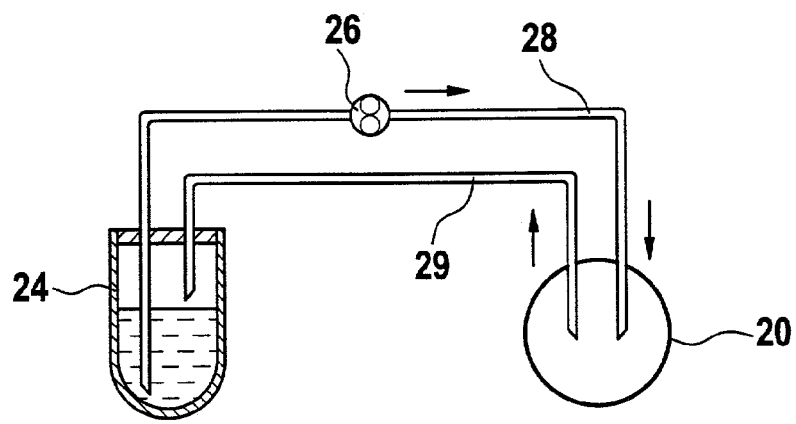
FIGS. 5a–5d show a variety of possible pumping arrangements.

In FIGS. 5a a single pumps means 26 is used with the microchip 20 shown in FIG. 2. The pump means is preferable a peristaltic pump. In operation the peristaltic pump causes liquid to flow from the external reservoir 24 into the microchip 20 and back out of the microchip into the external reservoir. The single pump and sealed microchip ensuring a constant volume is maintained in the microchip well.

Figure 5B:
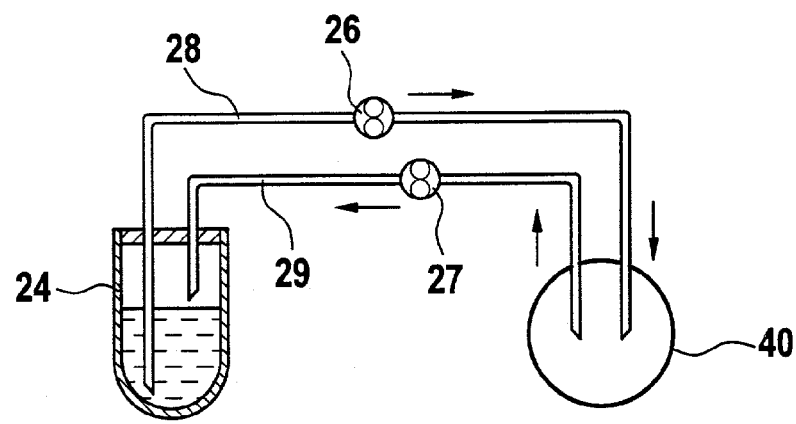

In FIGS. 5b two peristaltic pumps 26, 27 are employed with microchip 40 shown in FIG. 4. The first pump 26 operates to pump liquid from the external reservoir to the microchip, while the second pump 27 operates to pump liquid from the microchip to the external reservoir. By controlling the pump rates of the two pumps the volume of liquid in the microchip well can be controlled. For example, if both pumps are pumping at the same flow rate, the volume in the microchip well will remain substantially constant. However, if second pump 27 is operating at a higher flow rate than first pump 26, the volume of liquid in the microchip well will decrease.

Figure 5C:
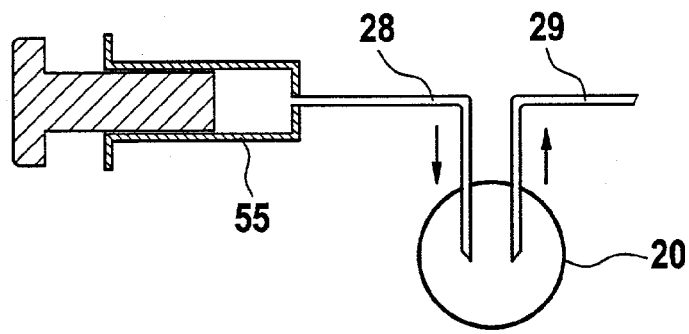

In FIG. 5c a syringe pump 55 is used in replacement of the peristaltic pump 26 of FIG. 5a.

Figure 5D:
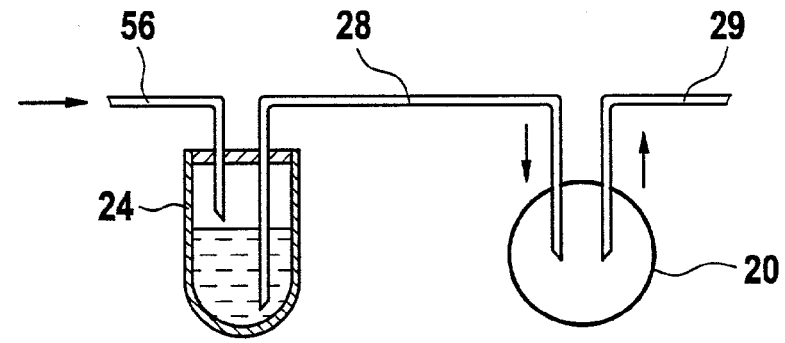

In FIG. 5d pumping is achieved by means of inputting a gas, such as Nitrogen or Helium, under pressure into the external reservoir 24 via a gas inlet line 56. As pressure increases in the external reservoir, liquid present in the reservoir is forced to flow from the reservoir via line 28 into the microchip and ultimately out of the microchip via line 29.

As will be appreciated, other pumping means could be used in addition to the examples given above without departing from the scope of the present invention.

In yet a further embodiment of the present invention, several possible arrangements of microchip wells and microchannels are disclosed.

Figure 6A:
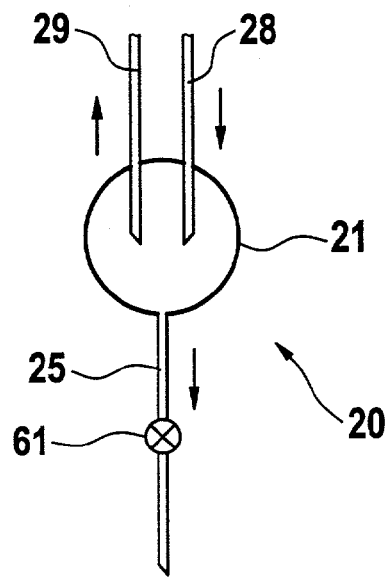
FIG. 6a shows a single microchannel and reservoir arrangement on the microchip.

In FIG. 6a microchip 20 is shown comprising a single microchip well 21 with input and output lines 28, 29 and a single microchannel 25. Sample and/or reagent is pumped into the microchip well 21 and caused to flow through the microchannel 25 by known methods such as electrophoresis or electroosmosis. Alternatively, flow through the microchannel can be driven by a vacuum pump disposed at the end of the microchannel. At detection point 61 located along microchannel 25 analysis of the sample occurs. Such analysis can be by any one of a variety of known techniques such as fluorescence, absorption, or electrochemical analyses.

Figure 6B:
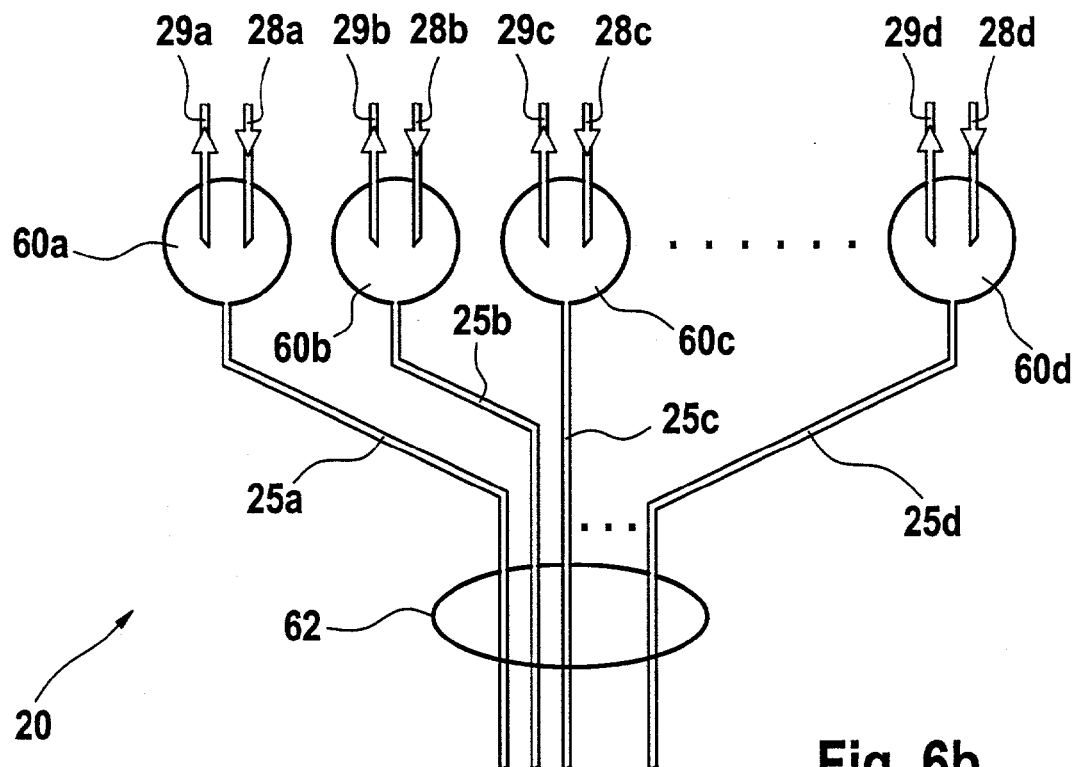
FIG. 6b shows a multiple microchannel and reservoirs arrangement on the microchip.

In FIG. 6b, a plurality of microchip wells 60a–60d are disposed on the microchip, each with a microchannel 25a–25d, an input line 28a–28d and an output line 29a–29d respectively. Similar to the arrangement described above for FIG. 6a, on-chip analysis occurs at detection area 62 located along microchannels 25a–25d.

Advantageously, by disposing a plurality of wells and channels on a single microchip, simultaneous multiple parallel on-chip detection is possible. The arrangement of wells and channels shown in FIG. 6b advantageously allows for faster sample throughput, thus reducing both cost and analysis time.

Figure 7A:
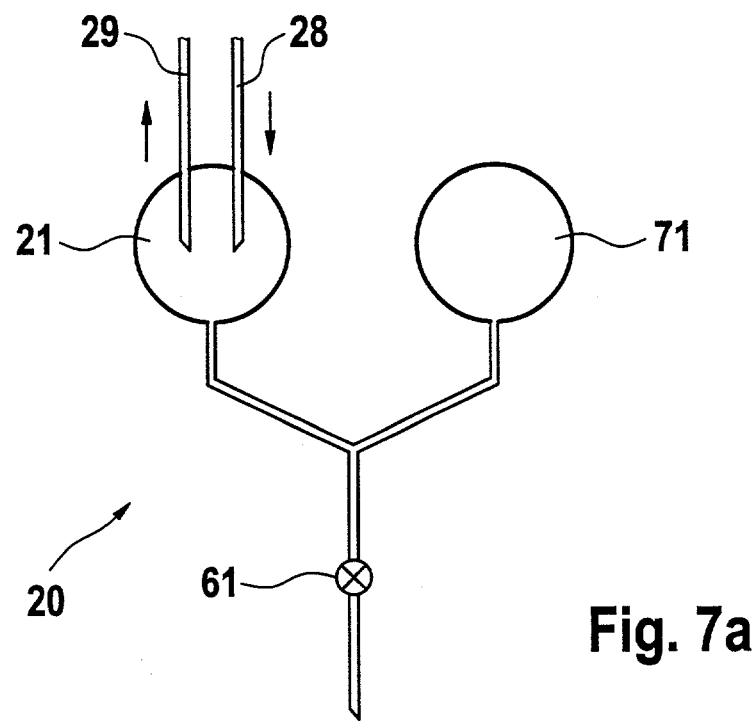
FIG. 7a shows a first possible measurement arrangement on the microchip.
Figure 7B:
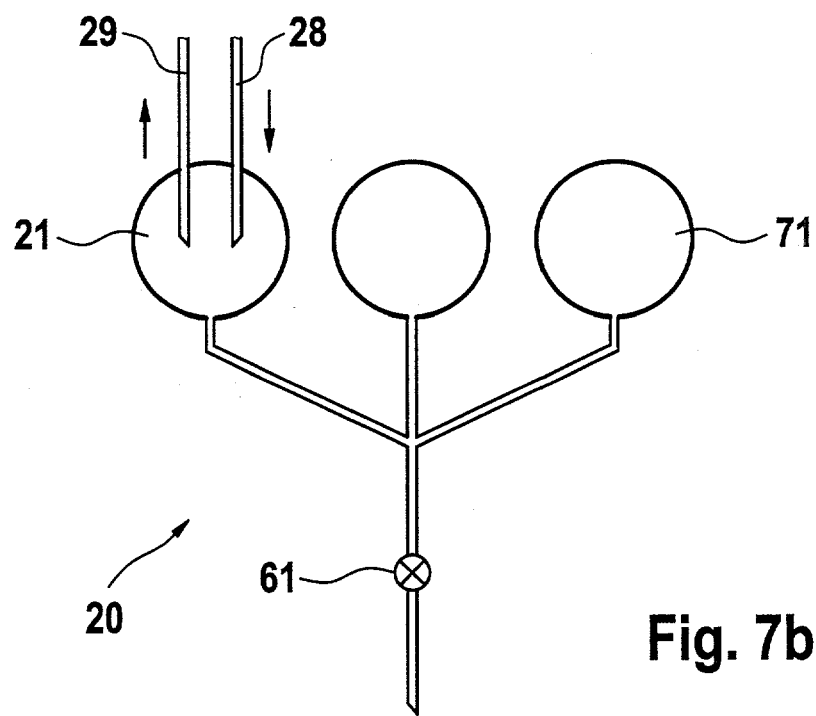
FIG. 7b shows a further possible measurement arrangement on the microchip.

It is possible to include further features on the microchip. In a further embodiment of the present invention, and as shown in FIGS. 7a and 7b, an on-chip reference well 71 is disposed on the microchip 20.

Advantageously, the presence of an on-chip reference allows for real time reference measurements to be taken under virtually the same experimental conditions as the sample measurements, thus improving the overall accuracy of the analysis.

Figure 8:
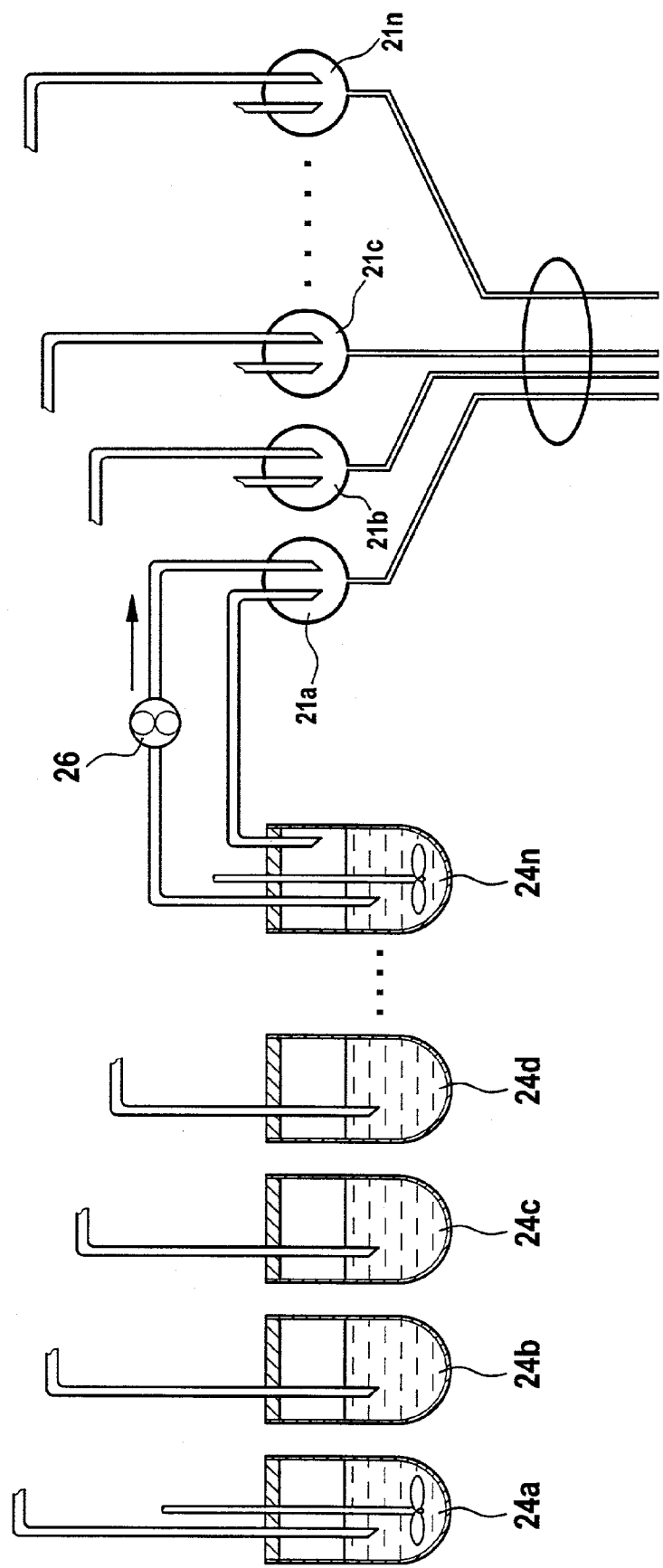
FIG. 8 shows a schematic of a possible on-line measurement system using the microchip and pumping arrangement of the present invention.

In yet a further possible embodiment of the present invention, and as shown in FIG. 8, the microchip shown in FIG. 6b can be incorporated with a plurality of external reservoirs 24a–24n and pumping means 26 to form an online parallel on-chip measurement system. Such a system may be used for dissolution testing, a tool well known within the pharmaceutical industry.

In addition to the above mentioned advantageously, the present invention allows for larger reservoir making the storage of greater quantities of reagents possible. The evaporation of liquid on-chip is reduced or eliminated, thus no concentration changes or reagent solutions occur during analysis. Reagents can be kept in external reservoirs at defined temperature which is important for cell assays and unstable enzymes. Cells do not need to be handled in a buoyancy adjusting buffer to avoid cell settling over measurement time. Viability and/or fluorescence label intensity of cells can be checked without interruption of a testing run.

Further advantages of the present invention are the ability for online replenishment of the microchip without having to refocus the optics, thus saving time, providing higher throughput, and reducing the danger of microchip being clogged by air bubbles or sedimented cells.

It is not intended that the present invention be limited to the above embodiments and other modifications and variations are envisaged within the scope of the claims.

The invention claimed is:

1. Measurement apparatus comprising:
    a microchip having (a) a well disposal therein, said well being capable of containing a volume of a liquid, and (b) a microchannel connected to said well and arranged to allow said liquid to flow therethrough;
    a reservoir disposed external to said microchip;
    an input line connecting said reservoir to said well and arranged to allow liquid to flow from said reservoir to said well;
    an output line connecting said well to said reservoir and arranged to allow liquid to flow from said well to said reservoir; and
    a pump disposed along said input line to facilitate (i) said flow of liquid from said reservoir to said well and (ii) said flow of liquid from said well.

2. Apparatus as claimed in claim 1, further comprising a lid hermetically disposed over said well, thereby sealing said well in an airtight manner.

3. Apparatus as claimed in claim 1, wherein said input line extends further into said well than does said output line.

4. Apparatus as claimed in claim 1, wherein said reservoir is hermetically sealed.

5. Apparatus as claimed in claim 1, wherein said input line extends further into said reservoir than does said output line.

6. Apparatus as claimed in claim 1,
wherein said pump is a first pump, and
wherein said apparatus further comprises a second pump disposed along said output line to facilitate said flow of liquid from said well to said reservoir.

7. Apparatus as claimed in claim 6, wherein said second pump comprises a peristaltic pump.

8. Apparatus as claimed in claim 6, wherein said second pump comprises a syringe pump.

9. Apparatus as claimed in claim 1, wherein said pump comprises inputting gas under pressure.

10. Apparatus as claimed in claim 1, wherein said microchip further comprises a plurality of wells and a plurality of microchannels.

11. Apparatus as claimed in claim 10, wherein at least one of said plurality of wells contains a reference sample.

12. Apparatus as claimed in claim 1, wherein said liquid comprises a solution containing proteins.

13. Apparatus as claimed in claim 1, wherein said liquid comprises a solution containing cells.

14. Apparatus as claimed in claim 1, wherein said pump is selected from the group consisting of a peristaltic pump and a syringe pump.

15. A method comprising:
connecting an input line from a reservoir to a well to allow liquid to flow from said reservoir to said well, wherein the reservoir is disposed external to a microchip having (a) the well disposed therein, wherein said well is capable of containing a volume of a liquid, and (b) a microchannel connected to said well and arranged to allow said liquid to flow there through;
connecting an output line from said well to said reservoir to allow liquid to flow from said well to said reservoir; and
facilitating said flow of liquid from said reservoir to said well and from said well to said reservoir by using a pump.

16. The method of claim 15, wherein at least one of said input line or said output line extend into said well.

17. The method of claim 15, wherein at least one of said input line or said output line extend into said reservoir.

18. The apparatus of claim 1, wherein at least one of said input line or said output line extend into said well.

19. The apparatus of claim 1, wherein at least one of said input line or said output line extend into said reservoir.

* * * * *